(12) United States Patent
Glenn et al.

(10) Patent No.: US 11,486,841 B2
(45) Date of Patent: Nov. 1, 2022

(54) SYSTEMS AND METHODS FOR MONITORING A GAS ANALYTE

(71) Applicant: Nexceris Innovation Holdings, LLC, Lewis Center, OH (US)

(72) Inventors: Bradley Glenn, Columbus, OH (US); Stephen Randall Cummings, Worthington, OH (US); Nicholas Brannigan Frank, Columbus, OH (US)

(73) Assignee: NEXCERIS INNOVATION HOLDINGS, LLC, Lewis Center, OH (US)

(*) Notice: Subject to any disclaimer, the term of this patent is extended or adjusted under 35 U.S.C. 154(b) by 0 days.

(21) Appl. No.: 17/602,227

(22) PCT Filed: Jun. 14, 2021

(86) PCT No.: PCT/US2021/037258
§ 371 (c)(1),
(2) Date: Oct. 7, 2021

(87) PCT Pub. No.: WO2021/257470
PCT Pub. Date: Dec. 23, 2021

(65) Prior Publication Data
US 2022/0099610 A1    Mar. 31, 2022

Related U.S. Application Data

(60) Provisional application No. 63/040,260, filed on Jun. 17, 2020.

(51) Int. Cl.
*G01N 27/02*  (2006.01)
*G01N 33/00*  (2006.01)

(52) U.S. Cl.
CPC ......... *G01N 27/02* (2013.01); *G01N 33/0027* (2013.01)

(58) Field of Classification Search
CPC .......................... G01N 27/02; G01N 33/0027
See application file for complete search history.

(56) References Cited

U.S. PATENT DOCUMENTS

2013/0197384 A1    8/2013   Tang et al.
2015/0303723 A1*  10/2015   Raghavan ............. H02J 7/0047
                                                         73/19.01
(Continued)

FOREIGN PATENT DOCUMENTS

CN    109271700 A  *  1/2019 ............. G06F 30/20
WO    2019/171363 A1    9/2019

OTHER PUBLICATIONS

International Search Report and Written Opinion in International Application No. PCT/US21/37258, dated Sep. 23, 2021 (7 pages).
(Continued)

*Primary Examiner* — Randy W Gibson
*Assistant Examiner* — John M Royston
(74) *Attorney, Agent, or Firm* — Benesch, Friedlander, Coplan & Aronoff LLP

(57) ABSTRACT

This disclosure relates to systems and methods for monitoring and classifying released gases in an enclosed system having a gas source, by a gas sensor that has been a priori pre-trained to distinguish an off-gas event (OGE) or a thermal run off event (TRE) from non-OGE interfering gases release. The pre-training utilizes one of a machine learning (ML) or a deep learning (DL) algorithm to pre-train the gas sensor to detect a plurality of known gas analyte to generate sensor signals with respective unique characteristics, extracting features from the sensor signals to establish a decision boundary or an estimated probability of a false positive release of the OGE or the TRE from the non-OGE type of interfering gas release. The established decision boundaries or probability distributions are implemented as
(Continued)

candidate model for field deployment to classify the released gases to distinguish whether OGE or TRE takes place.

15 Claims, 11 Drawing Sheets

(56) References Cited

U.S. PATENT DOCUMENTS

2018/0003685 A1* 1/2018 Cummings ........ G01N 33/0063
2019/0204281 A1* 7/2019 Choi .................... G01N 33/006

OTHER PUBLICATIONS

Badawa, D. et al., "Detecting Gas Vapor Leaks Using Uncalibrated Sensors," in IEEE Access, vol. 7, pp. 155701-155710, 2019 (10 pages).

"Chemical field-effect transistor," Wikipedia, 20903 [retrieved from the internet on Aug. 17, 2021 at <https://en.wikipedia.org/wiki/Chemical_field-effect_transitor>] (4 pages).

* cited by examiner

SYSTEMS AND METHODS FOR MONITORING A GAS ANALYTE

CROSS-REFERENCE TO RELATED APPLICATIONS

This application is a national stage entry of PCT International Patent Application No. PCT/US2021/037258, entitled "SYSTEMS AND METHODS FOR MONITORING A GAS ANALYTE", filed on Jun. 14, 2021, which claims priority to and the benefit from U.S. Provisional Patent Application No. 63/040,260 entitled "SYSTEMS AND METHODS FOR MONITORING A GAS ANALYTE", filed on Jun. 17, 2020. This application also makes reference to U.S. patent application Ser. No. 15/637,381, entitled "SYSTEMS AND METHODS FOR MONITORING FOR A GAS ANALYTE, filed on Jun. 29, 2017, and issued as U.S. Pat. No. 10,877,011B2 on Dec. 29, 2020, which claims the benefit of U.S. Provisional Application No. 62/356,111 filed on Jun. 29, 2016, entitled "SYSTEMS AND METHODS FOR ANALYTE DETECTION AND CONTROL", and U.S. Provisional Application No. 62/454,516 filed on Feb. 3, 2017, entitled "SYSTEMS INCLUDING AN ENERGY STORAGE ENCLOSURE AND MONITORING THEREOF", the contents of which are herein incorporated by reference in their entireties.

TECHNICAL FIELD

This disclosure generally relates to systems and methods for monitoring and classifying released gases in an enclosed system having a gas source, by a gas sensor that have been a priori pre-trained to distinguish an off-gas event (OGE) or a thermal run off event (TRE) from non-OGE interfering gases release.

BACKGROUND

A battery is an electronic device that can store high density electrical energy. Like any batteries, thermal runaway event (TRE) condition may happen during discharging and charging. For example, thermal runaway can be initiated by a short circuit within a battery (e.g., a cell of the battery), improper battery use, physical abuse, manufacturing defects, or exposure of the battery to extreme external temperatures. Thermal runaway occurs when an internal reaction rate of the battery increases to a point that more heat can be generated than can be withdrawn, leading to a further increase in both the internal reaction rate and heat generated.

The effects of a thermal runaway condition can depend on battery type. For example, in flooded electrolyte batteries, such as lead acid batteries, the thermal runaway condition can cause an electrolyte to boil off, resulting in a hazardous electrolyte gas escaping, also known as off-gas event (OGE) into a surrounding environment. In sealed batteries, such as Lithium ion battery, which may be used in devices, such as electric cars, laptops, cell phones, and the like, the thermal runaway condition can cause an expansion, which can result in the sealed battery exploding and releasing the hazardous electrolyte gas into the surrounding environment or causing a fire hazard.

SUMMARY

This disclosure relates to systems and methods for monitoring and classifying released gases in an enclosed system having a gas source, by a gas sensor that have been a priori pre-trained to distinguish an off-gas event (OGE) or a thermal run off event (TRE) from non-OGE interfering gases release. The pre-training utilizes one of a machine learning (ML) or a deep learning (DL) algorithm to pre-train the gas sensor to detect a plurality of known gas analyte to generate sensor signals with respective unique characteristics, extracting features from the sensor signals to establish a decision boundary or an estimated probability of a false positive release of the OGE or the TRE from the non-OGE type of interfering gas release. The established decision boundaries or estimated probability may be implemented as candidate model for field deployment to classify the released gases being one or both of the OGE or the TRE to distinguish from the non-OGE type interfering gas release.

A method for monitoring and classifying released gases in an enclosed system having a gas source may include the steps of: monitoring the gas source for release of a gas analyte, by at least one gas sensor having one or more sensing electrodes, wherein the at least one gas sensor having been pre-trained a priori utilizing one of a Machine Learning (ML) or a deep learning (DL) algorithm before sensor's initial field deployment to classify the released gas analyte being an event including one or both of: an off gas event (OGE) or a thermal run away event (TRE) from a non-OGE interfering gas release.

In an example, the utilizing of the ML or DL algorithm to pre-train the at least one gas sensor a priori to classify the released gas analyte may include at least the steps of (1) training the at least one gas sensor to detect over a time duration, each and every of a plurality of known gas analyte, by each of the one or more sensing electrodes of the at least one gas sensor to generate respective sensor signals that represent unique characteristics of the each and every of the plurality of known gas analyte; (2) pre-processing over the time duration, the generated respective sensor signals in order to extract corresponding plurality of features of the each and every of the plurality of known gas analyte; (3) processing the extracted corresponding plurality of features to establish a decision boundary of false positive release for one or both of the OGE and TRE, and to establish respective decision boundary for remaining each and every non-OGE type of interfering gas release; and (4) storing the established decision boundaries in the ML or pretrained Neural Networks that provides an estimated probability DL algorithm into a memory as one or more candidate model for sensor's post field deployment in order to classify the gas analyte released by the gas source as being one or both of the OGE or the TRE from the non-OGE interfering gas release.

In another embodiment, a system for monitoring and classifying released gases in an enclosed system having a gas source may include an enclosure having a gas source, at least one gas sensor having one or more sensing electrodes that is deployed to monitor the gas source for release of a gas analyte, wherein the at least one gas sensor before the deployment, having been pre-trained a priori utilizing one of a Machine Learning (ML) or deep learning (DL) algorithm that is stored as program code in a memory for execution by a processor in order to detect and classify the released gas analyte being an event comprising one or more of: an off gas event (OGE), an interfering gas release event, and a thermal run away event (TRE).

In an example, the utilizing of the ML or DL algorithm to pre-train the at least one gas sensor a priori to classify the released gas analyte causes the processor to pre-train the at least one gas sensor before sensor's initial field deployment to perform: (1) detect over a time duration, each and every of a plurality of known gas analyte, by each of the one or more sensing electrodes of the at least one gas sensor to generate respective sensor signals that represent unique characteristics of the each and every of the plurality of known gas analyte; (2) pre-process over the time duration, the generated respective sensor signals in order to extract corresponding plurality of features of the each and every of the plurality of known gas analyte; (3) process the extracted corresponding plurality of features to establish a decision boundary of false positive release for one or both of the OGE and TRE, and to establish respective decision boundary for remaining each and every non-OGE type of interfering gas from the plurality of known gas analyte; and (4) store the established decision boundaries in the ML or DL algorithm into a memory as one or more candidate model for sensor's post field deployment in order to classify the gas analyte released by the gas source as being one or more of the OGE, interfering gas event and TRE.

The disclosed system for monitoring and classifying released gases in an enclosed system having a gas source, by a gas sensor that have been a priori pre-trained to distinguish an off-gas event (OGE) or a thermal run off event (TRE) from non-OGE interfering gases release may be implemented as a non-transitory memory to store machine readable instructions. A processor may access the non-transitory memory and execute the machine readable instructions on a machine to carry out steps including: monitoring the gas source for release of a gas analyte, by at least one gas sensor having one or more sensing electrodes, wherein the at least one gas sensor having been pre-trained a priori utilizing one of a Machine Learning (ML) or a deep learning (DL) algorithm before sensor's initial field deployment to classify the released gas analyte being an event including one or both of: an off gas event (OGE) or a thermal run away event (TRE) from a non-OGE interfering gas release.

In an example, the machine readable instructions may utilize the ML or DL algorithm to pre-train the at least one gas sensor a priori to classify the released gas analyte may include at least the steps of (1) training the at least one gas sensor to detect over a time duration, each and every of a plurality of known gas analyte, by each of the one or more sensing electrodes of the at least one gas sensor to generate respective sensor signals that represent unique characteristics of the each and every of the plurality of known gas analyte; (2) pre-processing over the time duration, the generated respective sensor signals in order to extract corresponding plurality of features of the each and every of the plurality of known gas analyte; (3) processing the extracted corresponding plurality of features to establish a decision boundary of false positive release for one or both of the OGE and TRE, and to establish respective decision boundary for remaining each and every non-OGE type of interfering gas release; and (4) storing the established decision boundaries in the ML or DL algorithm into a memory as one or more candidate model for sensor's post field deployment in order to classify the gas analyte released by the gas source as being one or both of the OGE or the TRE from the non-OGE interfering gas release.

DETAILED DESCRIPTION

Figure 1:
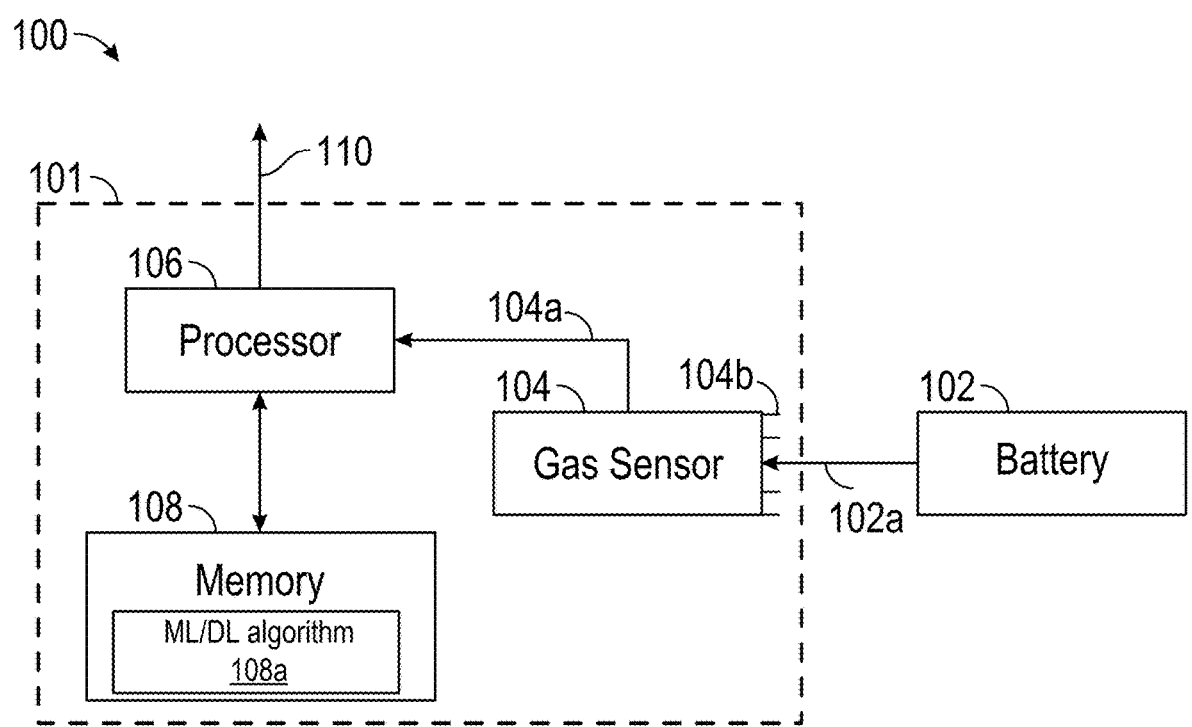
FIG. 1 depicts an example of a system 100 for monitoring an off-gas event (OGE).

This disclosure generally relates to systems and methods for monitoring an enclosed system having a gas source (e.g., a battery) for anyone of: an off-gas event (OGE), a thermal run away event (TRE) and an interfering (non-OGE) gas event, by at least one gas sensor which had been pre-trained a priori before initial deployment in the field (i.e., pre-trained in the factory), such that the deployed gas sensor requires no further need of training in the field and no need of using a reference gas sensor to detect gas release events.

Batteries over their life span may degrade progressively, which may result in a reduced capacity, cycle life, and safety. A degrading battery may release a gas, which may be referred to as an "off-gas." In one example, the off-gas may be released by the battery during cycling conditions, such as charge and discharge cycles. One or more causes of battery degradation may include improper battery use, physical abuse, manufacturing defects, exposure of the battery to extreme external temperatures, overcharge, or the like.

The systems and methods described herein can detect the off-gas event (OGE) during a cycle condition and to provide an early warning of a thermal runaway event (TRE) condition. In one example, the early warning may include a logic signal output, an audible alarm, a visual alarm, fire suppression, communication with other systems and a user. The off-gas detected during a cycle condition may be interpreted as a warning that the battery is at risk of thermal runaway. By providing an early warning, fires, explosions and injuries caused in response to a thermal runaway condition can be substantially mitigated. Furthermore, the systems and methods described herein can be configured to monitor any type of battery for the off-gas condition. Thus, the systems and methods described herein can be used to monitor a lithium ion battery, a lead-acid battery. In a broader application the systems and methods described herein may be applicable to any enclosed system having a gas source for detection of gas leakages of flammable or toxic gases, such as in a nuclear reactor environment, an oil or gas well drilling platform, a coal gas fired power generator, or the like.

The term "off-gas", "released gas" and "gas analyte" may be used interchangeably herein, and refers to a gas by-product of a chemical reaction of the gas source, such as the battery. An off gas (i.e., "released gas" and "gas analyte") can include an electrolyte gas, such as a volatile electrolyte solvent, a volatile component of an electrolyte mixture of the battery, or the like. Volatile electrolyte or off-gas analyte species may include at least the following flammable or toxic gases: lithium-ion battery off gas, dimethyl carbonate, diethyl carbonate, methyl ethyl carbonate, ethylene carbonate, propylene carbonate, vinylene carbonate, carbon dioxide, carbon monoxide, hydrocarbon, methane, ethane, ethylene, propylene, propane, benzene, toluene, hydrogen, oxygen, nitrogen oxides, volatile organic compounds, toxic gases, hydrogen chloride, hydrogen fluoride, hydrogen sulfide, sulfur oxides, ammonia, and chlorine or the like. In addition, the term "electrode" and "pad" may be used interchangeably to mean an electrically conductive terminal.

Moreover, the systems and methods described herein can be configured with a plurality of battery enclosures. Thus, the systems and methods described herein can be used to monitor for a gas analyte ("off-gas") released by one or more batteries located within a battery enclosure. The term "battery enclosure" as used herein refers to any housing that can partially encapsulate the one or more batteries. In an example, the battery enclosure can include a ventilated and non-ventilated battery enclosure. The ventilated battery enclosure can include a ventilation system that can include an intake and an exhaust. In an even further example, the battery enclosure can include a battery shipping container.

Moreover, the term "processor" as used herein can refer to any device capable of executing machine readable instructions, such as a computer, controller, an integrated circuit (IC), a microchip, or any other device capable of implementing logic. The term "memory" as used herein can refer to a non-transitory computer storage medium, such as volatile memory (e.g., random access memory), non-volatile memory (e.g., a hard disk drive, a solid-state drive, flash memory or the like) or a combination thereof.

FIG. 1 illustrates an example of a system 100 for monitoring an off-gas event (OGE). The system 100 includes at least a gas source such as a battery 102 and at least a gas sensor 104 deployed to monitor release of gas analyte 102a from the battery 102. The battery 102 may be a Li-ion battery having an enclosure (i.e., encapsulated with a protective case). In an embodiment, the gas sensor 104 may be a semiconductor type gas sensor or any suitable gas sensor that detects a gas analyte 102a (e.g. chemical vapor) released from the battery 102.

Unlike most other system, the deployed gas sensor 104 eliminates a requirement of using a separate reference sensor in the system 100 to calculate a moving average from the real time sensor signal 104a for a detection of an off gas event (OGE) in the battery 102. In implementation, the gas sensor 104 may be a sensor having one or more sensing electrodes 104b, and having been pre-trained a priori (e.g., during manufacturing) using one of a Machine Learning (ML) or a deep learning (DL) algorithm 108a (program code) stored in a memory 108 to be executed by a processor 106 to enable the gas sensor 104 to detect and classify in real time, any released gas analyte 102a as being an event comprising one or more of: an off gas event (OGE), a thermal run away event (TRE), and an interfering gas release event (i.e., non-OGE). In an example, the gas sensor 104, the processor 106 and the memory 108 may be an integrated chip 101, such as an ASIC semiconductor chip. In other examples, the gas sensor 104, the processor 106 and the memory 108 may each be discrete components electrically connected through a wiring harness or mounted on a printed circuit board (PCB).

The pre-trained gas sensor 104 may store the ML or DL algorithm 108a as a candidate model in the memory 108 to distinguish the sensor signals 104a detected by the gas sensor 104 as being one of an OGE and TRE from a non-OGE interfering gas event, without any need of a reference gas sensor or any further need of re-training the gas sensor 104 once deployed in the field.

The machine learning and training of the algorithm 108a steps may be performed a priori in the factory during the manufacturing process, or off-line at any time, prior to physical commissioning or installing of the sensor 104 in the system 100. No real-time adaption would be necessary once the sensors 104 are commissioned in the system 100. Yet alternately in another option, the ML or DL algorithm 108a may be re-trained or updated by the sensor 104 to learn new encounters to other gas analyte which had not been pre-retrained or listed in a database. The goal of this pre-training using the ML or DL algorithm is not only to detect an OGE, but also be able to identify other gas sources detected by the sensor 104, thus eliminating the need for a reference sensor.

In an example, the priori pre-training utilizing the ML or DL algorithm 108a on the at least one gas sensor 104 may include at least the steps of: (1) training the at least one gas sensor to detect over a time duration, each and every of a plurality of known gas analyte (i.e., training gases), by each of the one or more sensing electrodes 104b of the at least one gas sensor 104 to generate respective sensor signals 104a that represent unique characteristics of the each and every of the plurality of known gas analyte for establishing a database; (2) pre-processing over the time duration, the generated respective sensor signals 104a in order to extract corresponding plurality of features (e.g., impedances and capacitance, see FIGS. 3A,B to 7) of the each and every of the plurality of known gas analyte 102a, (3) processing the extracted corresponding plurality of features to establish a decision boundary (see FIGS. 9 and 10) of false positive release for one or both of the OGE and TRE, and to establish respective decision boundary for remaining each and every non-OGE type of interfering gas release; and (4) storing the established decision boundaries in the ML or DL algorithm (108a) into a memory 108 as one or more candidate model for sensor's post field deployment in order to classify the gas analyte 102a released by the gas source (e.g., battery 102) as being one or both of the OGE or the TRE from the non-OGE interfering gas release. An output signal 110, such as an alert alarm or a logic signal may be sent for warning or for display on a screen to take preventive measure from causing an accident or damage to the system 100.

In an example, the gas source may be a rechargeable Lithium ion battery system or an electric energy storage system 102, wherein the gas analyte released in the OGE or the TRE may be one or a combination of at least the following flammable or toxic gases: lithium-ion battery off gas, dimethyl carbonate, diethyl carbonate, methyl ethyl carbonate, ethylene carbonate, propylene carbonate, vinylene carbonate, carbon dioxide, carbon monoxide, hydrocarbon, methane, ethane, ethylene, propylene, propane, benzene, toluene, hydrogen, oxygen, nitrogen oxides, volatile organic compounds, toxic gases, hydrogen chloride, hydrogen fluoride, hydrogen sulfide, sulfur oxides, ammonia, and chlorine, to name a few.

Figure 2:
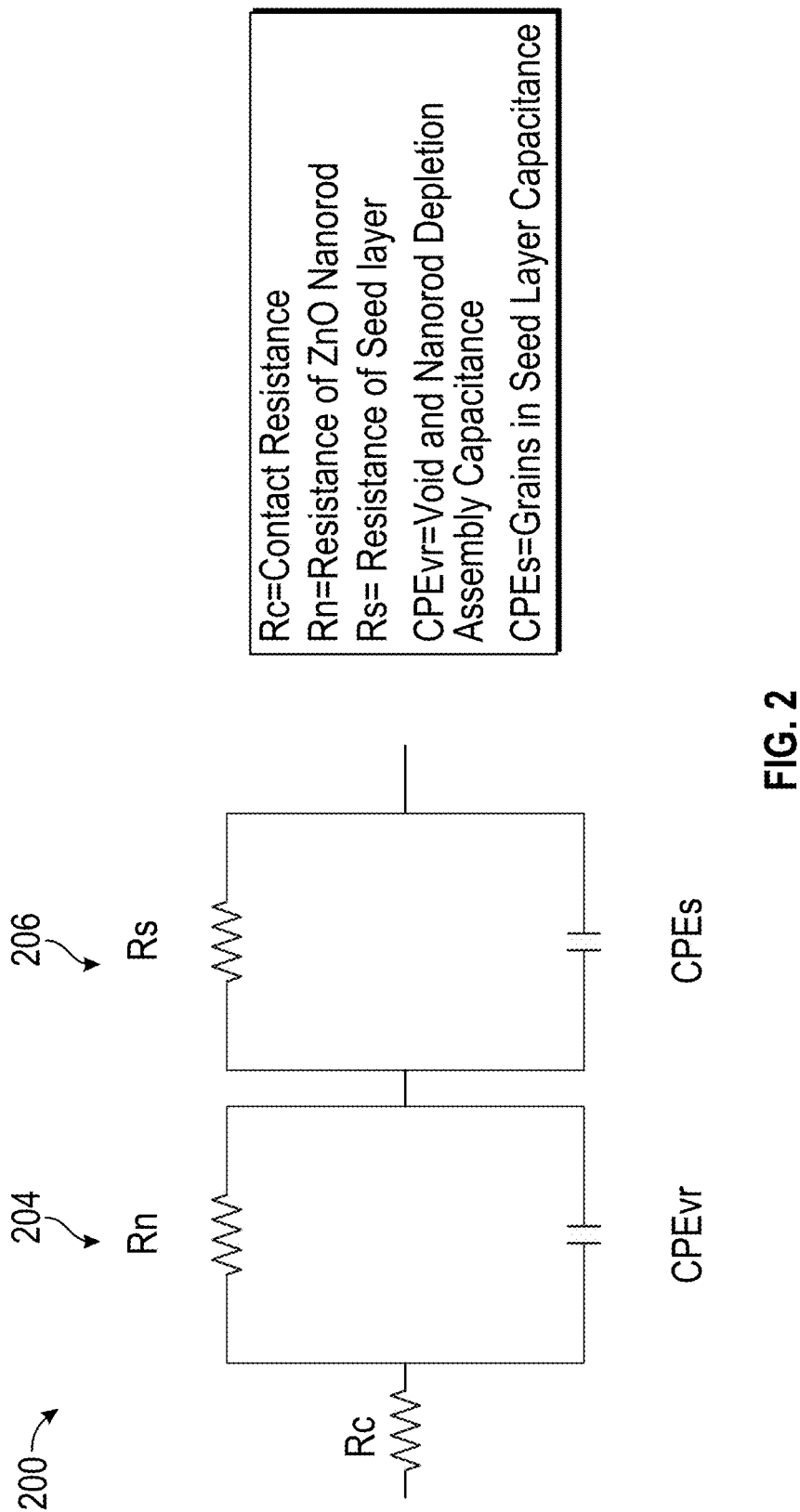
FIG. 2 depicts an example of an equivalent electrical circuit model of a gas sensor which simulates monitoring and detection of events including an off-gas event (OGE), a thermal run away event (TRE) and an interfering (non-OGE) gas event.

In practice, the ML or DL learning method during the pre-training may be based on an equivalent circuit model 200 of the sensor 104 as shown in FIG. 2. For illustration, FIG. 2 may represent an equivalent circuit model of a semiconductor gas sensor. However, other gas sensors may use other equivalent circuit models to be expressed with another transfer function. The illustrated gas sensor type and equivalent circuit model example are non-limiting.

The equivalent impedance circuit model 200 in FIG. 2 shows that the respective gas sensor signals generated by each of the one or more sensing electrodes 104b of the at least one gas sensor 104 may include impedance values based on a first parallel resistor Rn and capacitor CPEvr pair 204 cascading in series with a second parallel resistor Rs and capacitor CPEs pair 206. The first parallel resistor and capacitor pair 204 in the equivalent circuit model 200 may simulate dynamics of the at least one gas sensor responses 104a which may be exposed to a combination of different released analyte gases 102a. The impedance equivalent circuit model 200 of the sensor 104 further includes cascading in series, a contact resistance Rc to the first parallel resistor Rn and capacitor CPEvr pair 204.

Given an output impedance, R, a gas sensor 104 having a fixed input voltage V in the LaPlace domain (s), a corresponding input/output transfer function may be developed for the equivalent circuit model 200, which may be expressed as follows:

$$\frac{R}{V}(s) = \frac{(CPE*CsRnRs)s^2 + (CPE*Rn + Cs*Rs)s + 1}{CPE*C_sR_cR_nR_ss^2 + (CPE*RcRn + CPE*RnRs + CsRcRs + CsRnR)s + Rc + Rn + Rs}$$

wherein Rc is a contact resistance, Rn and Rs are resistances of the circuit model, CPEvr and CPEs are capacitances of gains in the circuit model.

The changes in impedance values (i.e., resistance and capacitance) over time (see FIGS. 3A,B to 7) from the electrical elements (Rc, Rn, Rs, CPEvr, CPEs) caused by each and every of the plurality of known gas analyte 102a in the circuit model 200 may be transmitted as sensor signals 104a for training, representing unique characteristics or properties of the detected known gas analyte. The ML or DL learning method simulates monitoring and detection of the detected gas analyte 102a released from the gas source (i.e., battery 102), thus classifying the gas release events as being one or a combination of: an off-gas event (OGE), a thermal run away event (TRE) and an interfering (non-OGE) gas event. The known gas analyte may be the gases mentioned in the OGE or the TRE for training, including but not limited to at least the following flammable or toxic gases: lithium-ion battery off gas, dimethyl carbonate, diethyl carbonate, methyl ethyl carbonate, ethylene carbonate, propylene carbonate, vinylene carbonate, carbon dioxide, carbon monoxide, hydrocarbon, methane, ethane, ethylene, propylene, propane, benzene, toluene, hydrogen, oxygen, nitrogen oxides, volatile organic compounds, toxic gases, hydrogen chloride, hydrogen fluoride, hydrogen sulfide, sulfur oxides, ammonia, and chlorine, to name a few.

In an example, a mathematical representation using estimation techniques of such as least-squares methods, and gradient algorithm may be used to extract the equivalent resistances and capacitances in the equivalent model 200 of the gas sensor 104. In practice, the ML or DL algorithm pre-training of the at least one gas sensor 104 in detecting release of the gas analyte 102a may include distinguishing the sensor impedance changes due to environmental disturbances caused by one or more of: temperature changes, relative humidity changes, and other gases that effects a partial pressure of oxygen in the environment that leads to reporting a false positive.

Figure 11A:
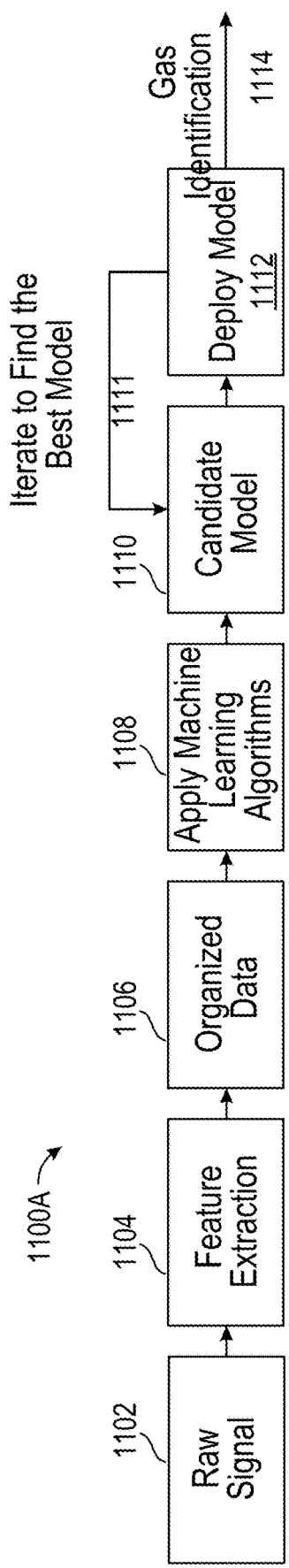
FIGS. 11A and 11B depict an exemplary gas sensor pre-training flow diagram applying a Machine Learning (ML) or a Deep Learning (DL) algorithm.
Figure 11B:
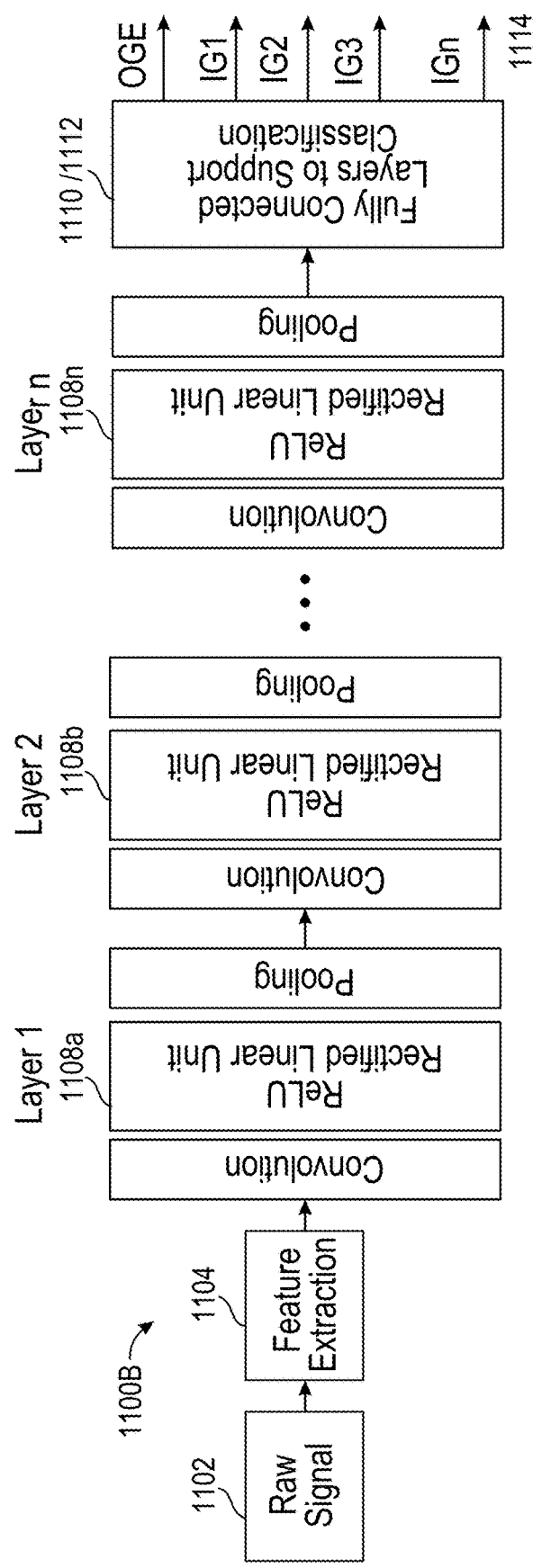
Figure 12:
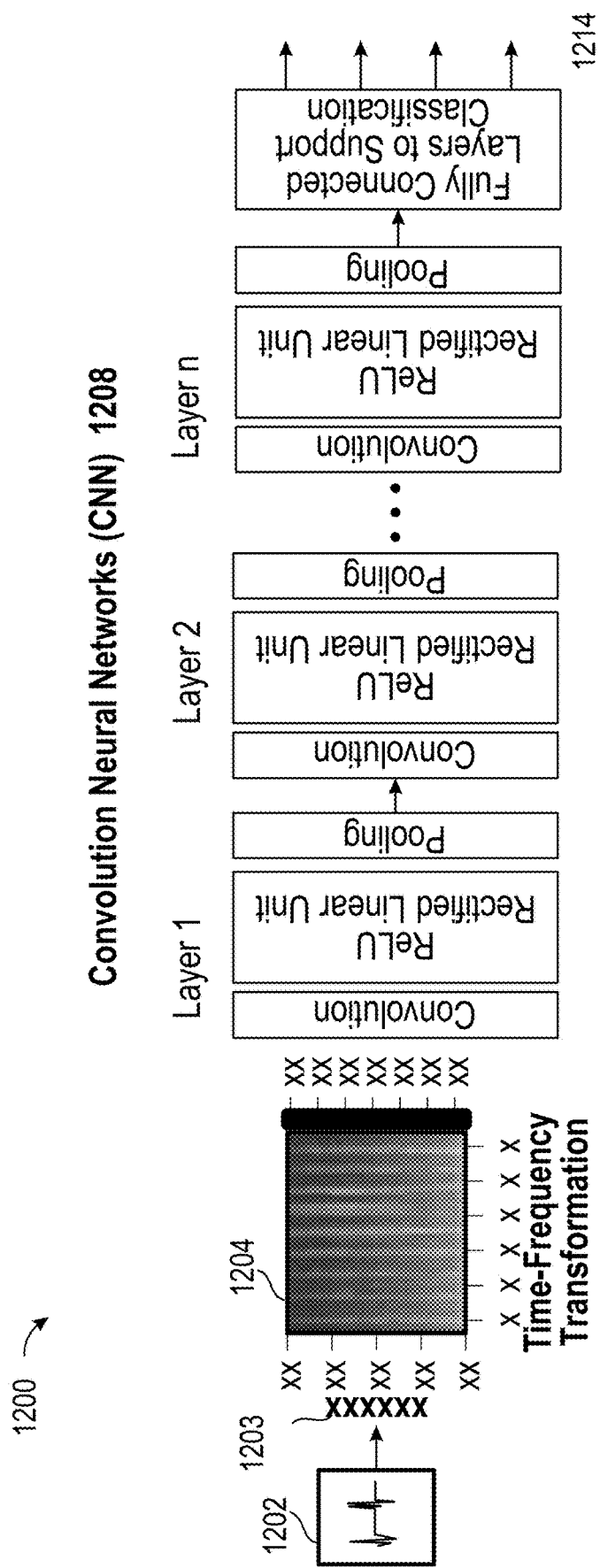
FIG. 12 depicts implementing a Convolutional Neural Network in Deep Learning (DL) training.

In an example, the ML algorithm pre-training (see FIG. 8) of the at least one gas sensor 104 in the extraction of the corresponding plurality of features of the each and every of the plurality of known gas analyte may include utilizing anyone or a combination of features comprising: moving average calculation, Bollinger band, minimum electrode impedance, maximum rate of impedance change, maximum rate of recovery of impedance for each of the at least one electrodes 104b on the at least one gas sensor 104, principal component analysis (PCA), linear discriminant analysis, wherein the DL algorithm pre-training of at least at least one gas sensor in the extraction of the corresponding plurality of features in the each and every of the plurality of known gas analyte are contained internally in hidden layers of DL Neural Networks (see FIGS. 11A, 11B and 12).

In another example, the ML or DL algorithm pre-training of the at least one gas sensor in the establishing of the decision boundary of false positive release for the OGE or the TRE and respective decision boundary for the remaining each and every type of non-OGE interfering gas release, may include evaluating the generated sensor signals 104a utilizing anyone of determination methods including: Support Vector Machines, Discriminant Analysis or nearest neighbor algorithm, Naïve Bayes and Neural Neighbor, Linear Regression, GLM, Support Vector Regression, GPR, Ensemble Methods, Decision Trees, and DL Neural Networks including at least one of: Convolution Neural Networks (CNN) (FIG. 12) and Long Short Term Memory (LSTM) Networks (FIGS. 11A, 11B).

Figure 3A:
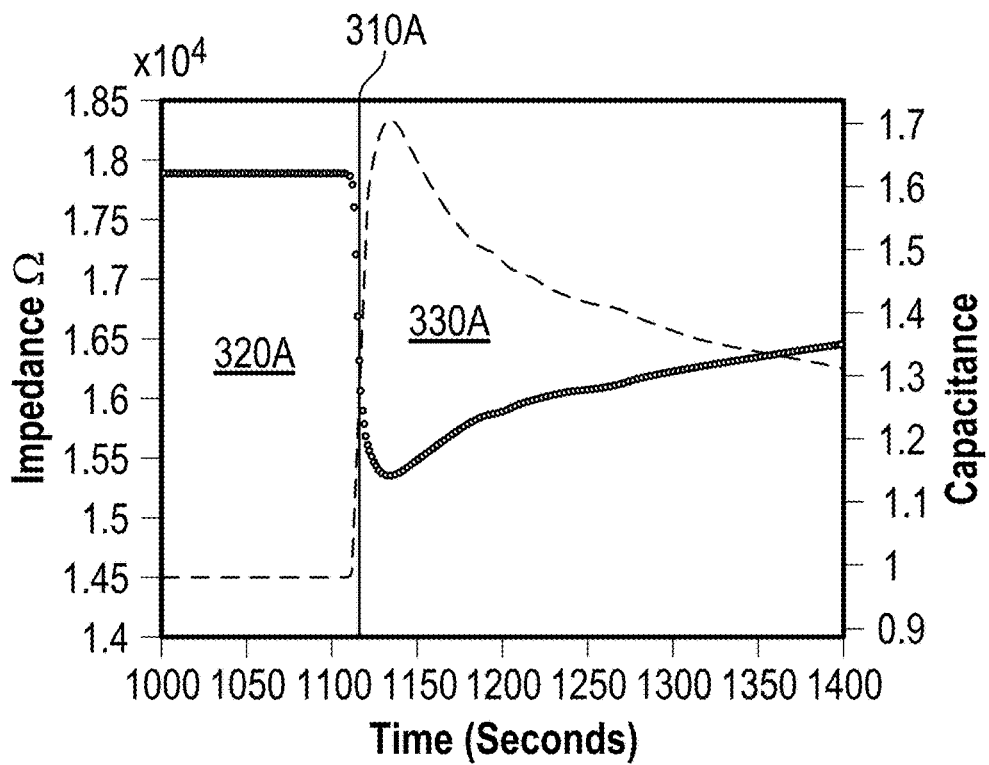
FIGS. 3A and 3B illustrate two separate off-gas events which are depicted as impedance and capacitance changes to be extracted as ML features from the equivalent electrical circuit model of a gas sensor as shown in FIG. 2.
Figure 3B:
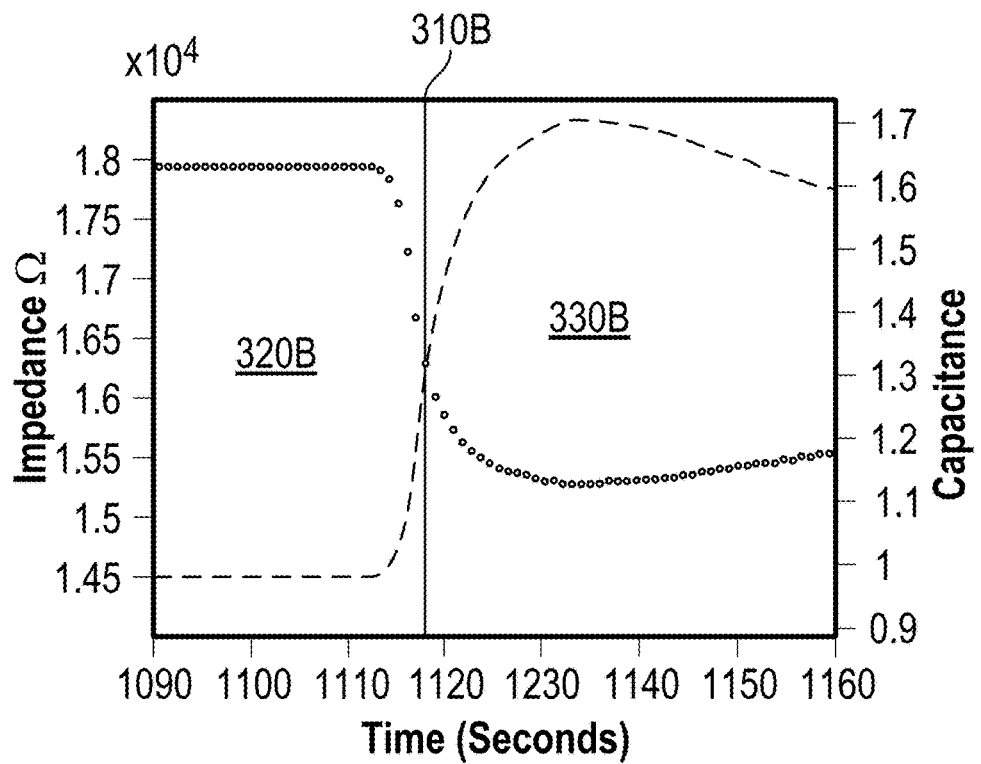

FIGS. 3A and 3B illustrate two separate off-gas events from the received sensor signals 104a, which are depicted as impedance and capacitance changes (e.g., abrupt change from region 320A to region 330A in FIG. 3A, region 320B o 330B in FIG. 3B) over a time duration to be extracted as ML features from the equivalent electrical circuit model of a gas sensor 104 as shown in FIG. 2. These data may be training parameters for the ML and DL machine learning algorithm for establishing a decision boundary (see FIGS. 9, 10).

Figure 4:
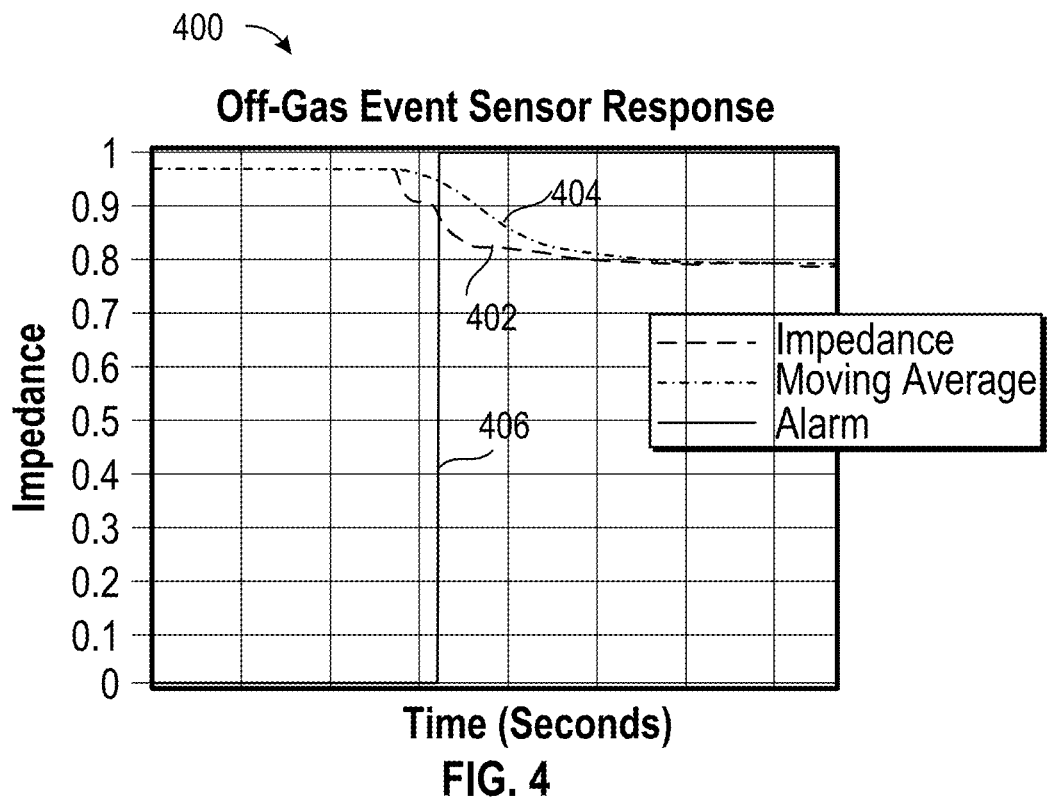
FIG. 4 depicts an example of an OGE for a single electrode gas sensor from an OGE gas source.
Figure 5:
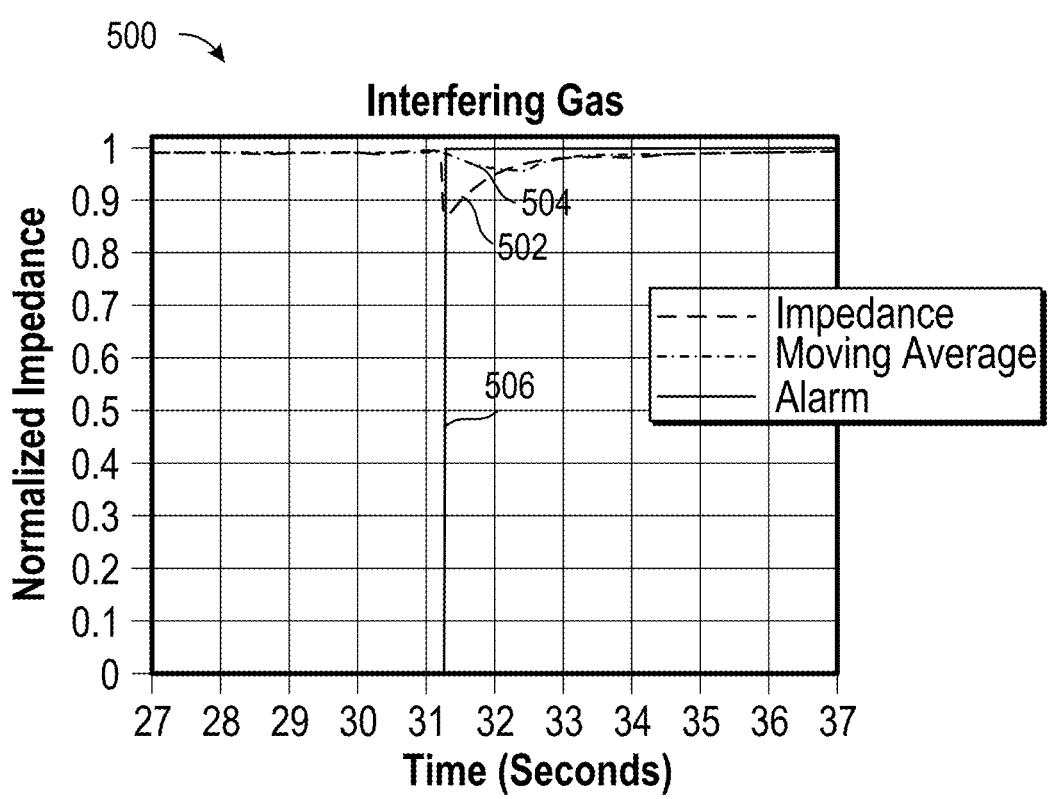
FIG. 5 depicts an example of a false positive detection from an interfering gas source for a single electrode gas sensor with existing algorithm.

FIG. 4 depicts an example of an OGE for a single electrode gas sensor 104 from an OGE gas source. In an example, the sensor signals 104a parameters may include at least the changes over a time duration on values of impedance, moving average which may cause generation of an alarm in output signal 110. Likewise, FIG. 5 depicts an example of a false positive detection from an interfering gas source (non-OGE) for a single electrode gas sensor with existing algorithm.

Figure 6:
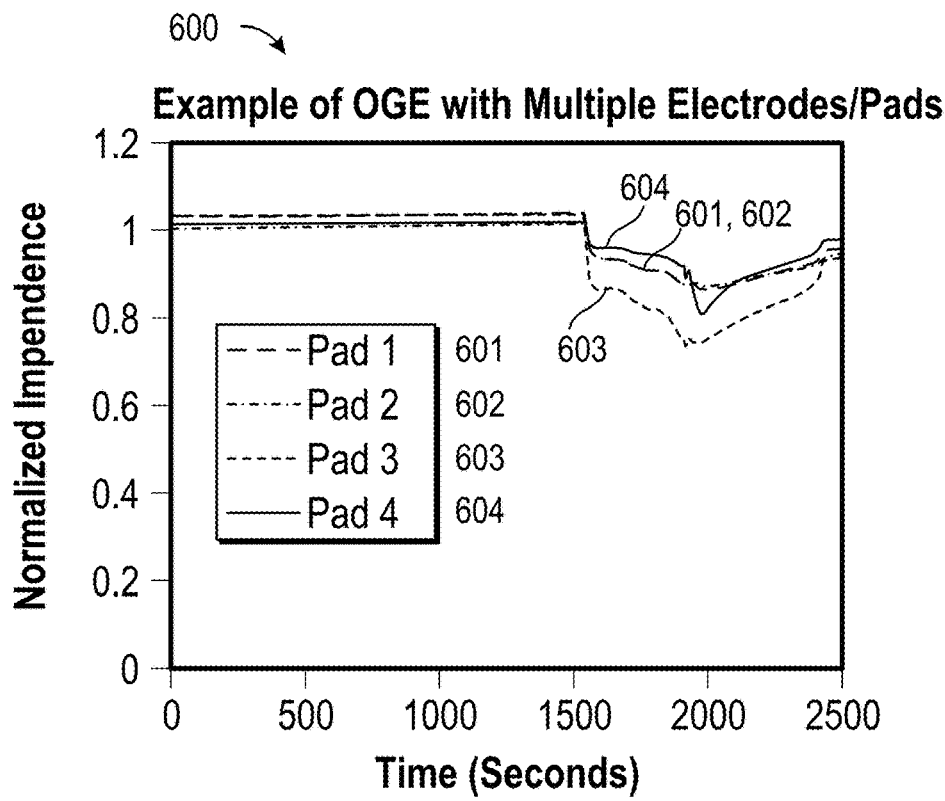
FIG. 6 depicts an example of an OGE for an at least one electrodes gas sensor from an OGE gas source.
Figure 7:
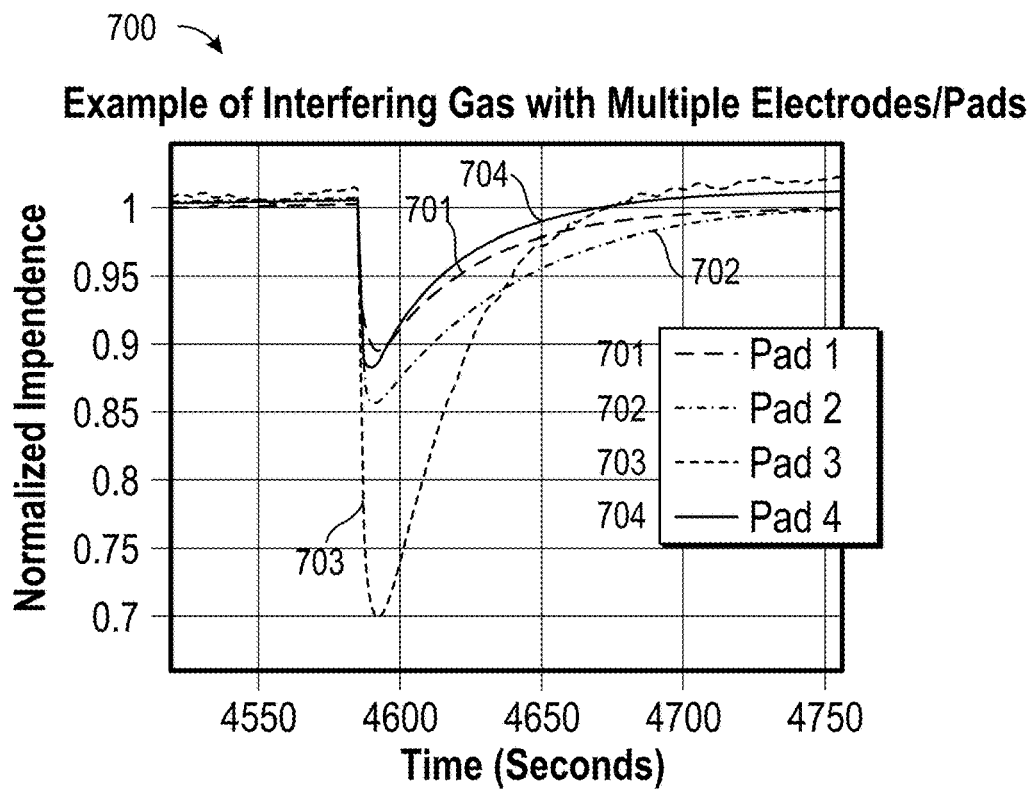
FIG. 7 depicts an example of an interfering gas event for an at least one electrodes gas sensor from for a non-OGE gas source.

FIG. 6 depicts an example of an OGE for an at least one electrodes gas sensor from an OGE gas source. FIG. 7 depicts an example of an interfering gas event for an at least one electrodes gas sensor from for a non-OGE gas source. The unique response of each electrode in the gas sensor provides the ML learning algorithm the ability to distinguish between an OGE and common interfering gases in an energy storage facility.

ML Algorithm has the unique selectivity that allows for the identification of an OGE as well as identifying which interfering gas is present to allow for other diagnostic capability. By comparison, the increase in number of electrodes 104b in a gas sensor 104, in effect, provides more unique responses which may be unique characteristics or attributes (e.g., finger prints) to help identity the detected gas analyte. Likewise, the extracted features from the one or more sensing electrodes may establish a one or more dimensional dynamic response in establishing more accurately the false positives decision boundaries of OGE, TRE and non-OGE type interfering gas events, therefore improving the reliability and accuracy (by reducing the probability of error) in the trained candidate model in identifying the type of gas analyte as well as in the event classification.

stationarity (e.g. sliding window measures, prediction errors), information theoretic and entropy/complexity etc.

Figure 8:
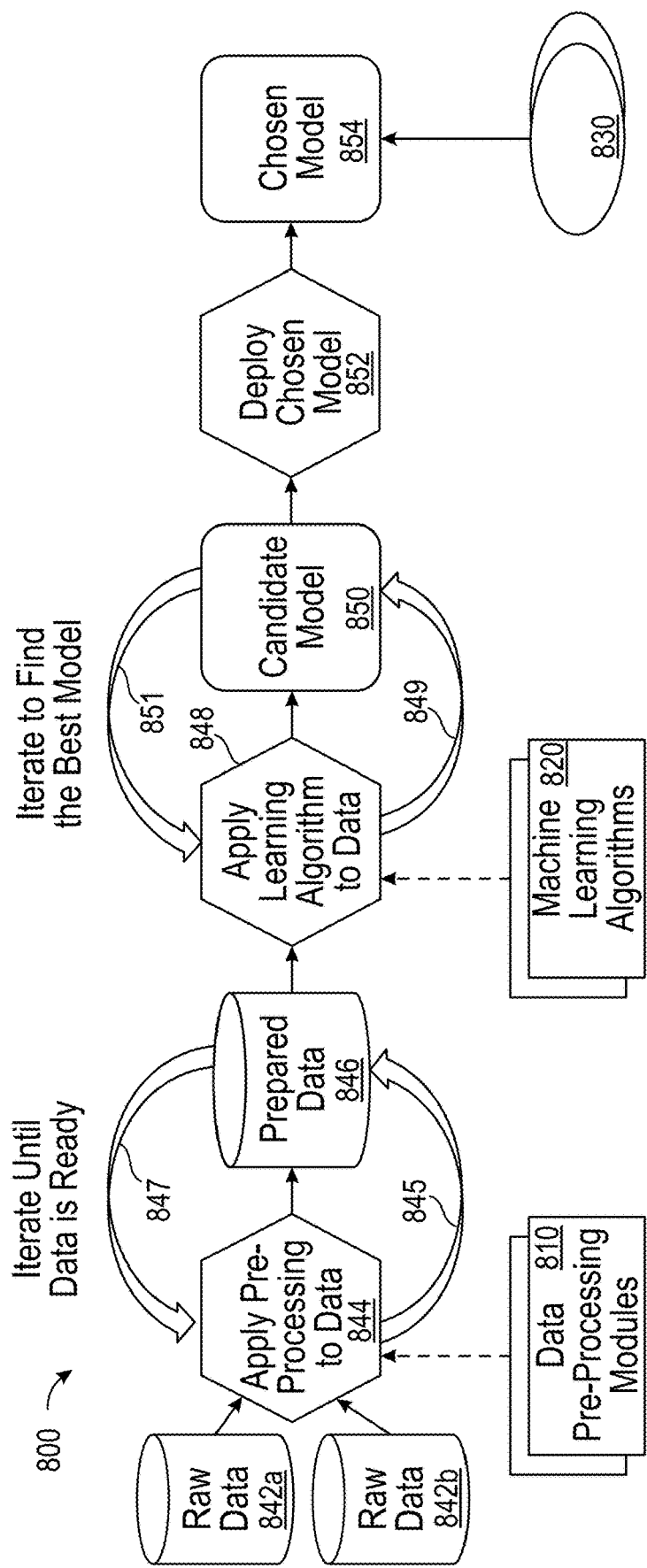
FIG. 8 depicts an example of a Machine Learning (ML) Classification design process.

Table 1 below provides some examples of the different features extracted from the sensor signals 104a in each of the multiple electrodes 104b, which may be utilized in the ML or DL algorithm 108a for a priori training and for establishing a decision boundary to classify the gas analyte 102a as being one of the OGE, TRE and non-OGE interfering gas event (as shown in the processes of FIGS. 8 and 11A, 11B). The machine learning is a supervised learning techniques may utilize linear regression, nearest neighbor, support vector regression, and neural networks in the training to establish a candidate model 854 for use when deploying the gas sensor 104 in the field.

TABLE 1

| Feature 1 | Feature 2 | Feature 3 | Feature 4 | Feature 5 | Feature 6 | Gas Type |
|---|---|---|---|---|---|---|
| 0.774691 | 0.701516 | 0.674988 | 0.866383 | −0.03044 | −0.03406 | Interfering Gas 1 |
| 0.829714 | 0.7555 | 0.838982 | 0.919975 | −0.07514 | −0.07582 | Interfering Gas 1 |
| 0.768456 | 0.697034 | 0.675138 | 0.87619 | −0.10458 | −0.11013 | Interfering Gas 1 |
| 0.920379 | 0.875693 | 0.958897 | 0.964187 | −0.02719 | −0.03223 | Interfering Gas 1 |
| 0.885411 | 0.821586 | 0.952449 | 0.961552 | −0.01485 | −0.01715 | Interfering Gas 2 |
| 0.827432 | 0.7544 | 0.833974 | 0.918782 | −0.06566 | −0.06751 | Interfering Gas 2 |
| 0.737762 | 0.672099 | 0.610817 | 0.843494 | −0.14042 | −0.13649 | Interfering Gas 2 |
| 0.778001 | 0.705386 | 0.698497 | 0.883416 | −0.09282 | −0.11494 | Interfering Gas 2 |
| 0.738887 | 0.67214 | 0.616065 | 0.849154 | −0.11429 | −0.11681 | Interfering Gas 3 |
| 0.78249 | 0.675069 | 0.699502 | 0.885526 | −0.09325 | −0.11944 | Interfering Gas 3 |
| 0.818389 | 0.713922 | 0.814425 | 0.91466 | −0.07889 | −0.11787 | Interfering Gas 3 |
| 0.774843 | 0.670419 | 0.692568 | 0.882074 | −0.13414 | −0.1787 | Interfering Gas 3 |
| 0.932275 | 0.864262 | 0.964597 | 0.978366 | −0.02777 | −0.04665 | OGE |
| 0.892163 | 0.806155 | 0.952128 | 0.969763 | −0.01669 | −0.02967 | OGE |
| 0.845022 | 0.743398 | 0.870444 | 0.934548 | −0.06587 | −0.08874 | OGE |
| 0.732432 | 0.63537 | 0.610214 | 0.839241 | −0.14826 | −0.20349 | OGE |

FIG. 8 depicts an example of a Machine Learning (ML) Classification design process or how the ML algorithm may be developed. The pre-training (supervised learning) approach may combine many signal features (from the gas sensor 104) using both heuristic and physics-based impedance information in the data pre-processing step of the algorithm development phase. It may also include environmental measurements such as Temperature, Pressure, Relative Humidity included in the sensor set offering. For example the signal features may include moving average, Bollinger band, minimum electrode impedance, maximum rate of impedance change, maximum rate of recovery of impedance for each electrode, principal component analysis (PCA), and linear discriminant analysis. Additionally, the pre-training (supervised learning) of the gas sensor to distinguish an OGE or TRE from a non-OGE using other techniques may also include, but is not limited to classification techniques such as: support vector machine, discriminant analysis or nearest neighbor algorithm, basic statistics of the distribution of time series values (e.g., location, spread, Gaussianity, outlier properties), linear correlations (e.g., autocorrelations, features of the power spectrum), Table 1 shows some examples of Extracted Features from each of the at least one electrodes for each gas type that have been mentioned in the previous section. The transformed data, are tabulated in the Table 1 with various features extracted from the raw data, which are used to create the candidate models using an optimization process that searches for model parameters, including using the fitting data and evaluates them using the test data not used for fitting, and tunes the candidate model until optimal performance may be achieved. Feature extraction in deep learning may be incorporated internal to the Neural Network (see FIGS. 11A, B, 12, 13 and 14A and 14B) and does not need to be carried out before classification.

In another example, as part of the pre-training process, the extracted features from the known gas analyte may be used to train the ML or DL algorithm to sufficiently quantify an approximate percentage % or parts per million ppm of each identified gas analyte in a detected gas analyte composition, which may be useful to help classify one of or a combination of the OGE, TRE and non-OGE as interfering gas release from the gas source. Table 2 below may illustrate some examples of the detected gas analyte compositions.

TABLE 2

| Gas composition |
|---|
| 36.2 v % carbon monoxide; |
| 22.1 v % carbon dioxide; |
| 31.7 v % hydrogen; |
| 10.0 v % hydrocarbons |
| Hydrocarbon breakdown |
| 7.4 v % methane; |
| 0.92 v % ethylene; |
| 0.61 v % ethane; |
| 0.22 v % propylene; |
| 0.04 v % propane; |
| 0.07 v % C4-hydrocarbons; |
| 0.24 v % benzene; |
| 0.03 v % toluene; |
| 0.38 v % dimethyl carbonate |

Figure 9:
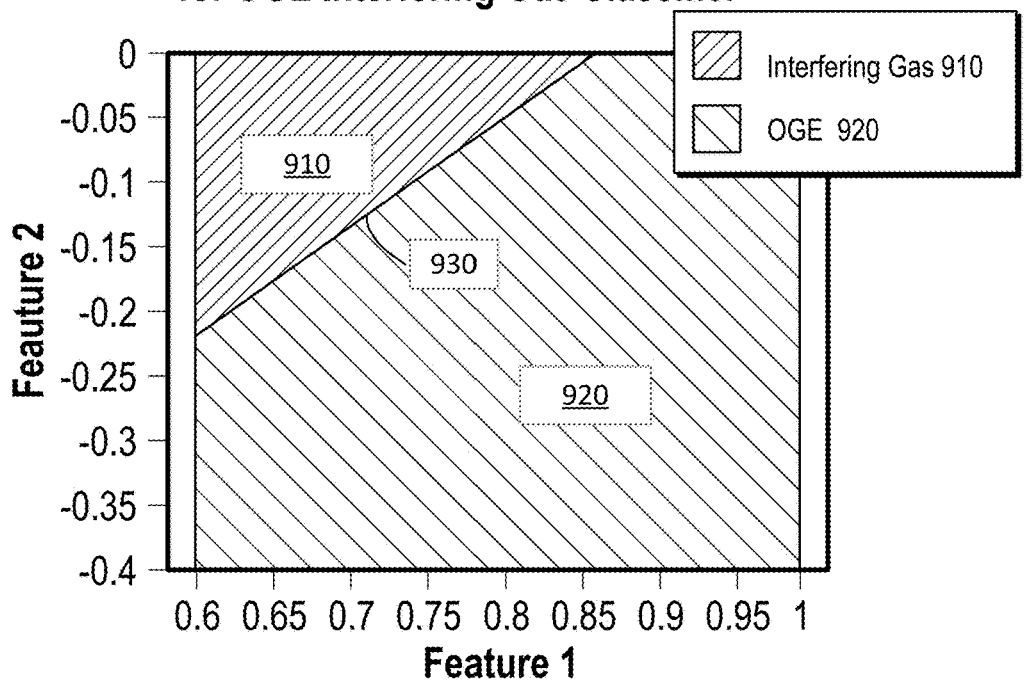
FIG. 9 depicts an example of a decision boundary separating a real OGE from a false OGE, which the decision boundary is established by the extracted features in a trained ML algorithm.

FIG. 9 depicts an example of a decision boundary 930 separating real OGE 910 from false OGE 920, which the decision boundary is established by the extracted features in a trained ML algorithm 108a over a historical time duration. Within the region 910 means OGE has been detected and within region 920 means a non-OGE. In reality the decision boundary 930 will be highly dimensional (i.e., much higher than three dimensions) based on time series data, making it almost impossible to depict all the decision boundary plots by the examples shown in FIGS. 9 and 10.

Figure 10:
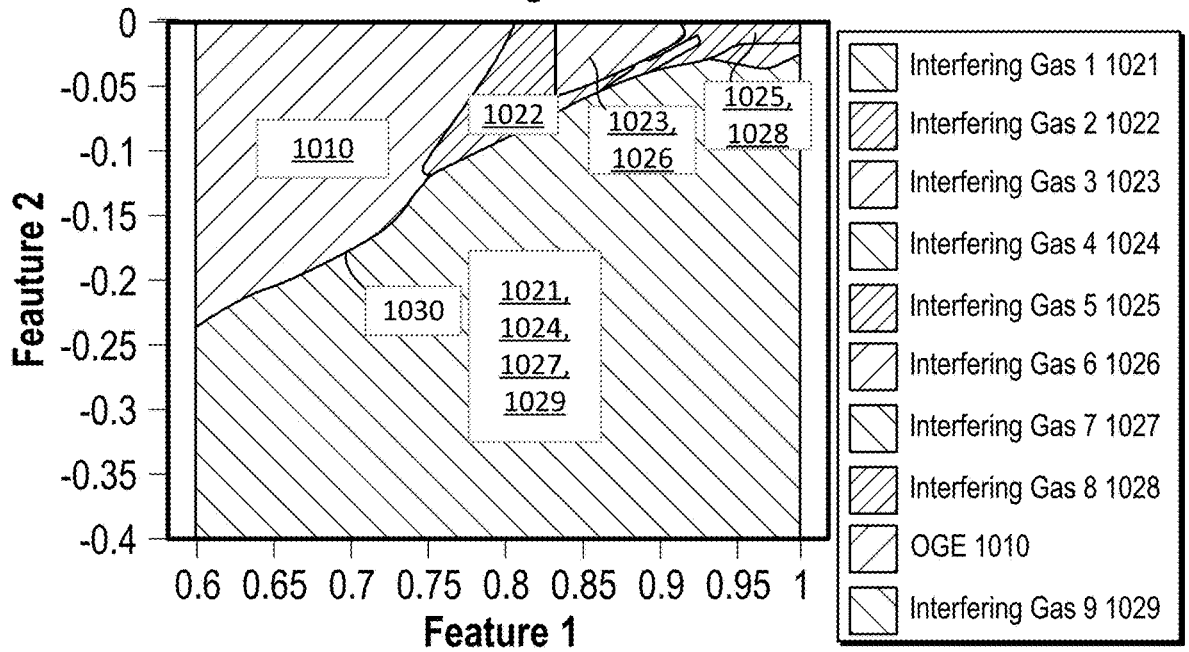
FIG. 10 depicts an example of real and false off-gas events and other gases selectivity in decision boundary trained with the ML algorithm.

FIG. 10 depicts an example of real OGE 1010 and false OGE and other gases (1021-1029) selectivity in decision boundary 1030 trained with the ML algorithm 108a. The ML or DL algorithm 108a may include a selectivity algorithm using the same idea of training a decision boundary using the similar process or techniques shown in FIG. 8, except that FIG. 8 may show a composite of several dimensions corresponding to other extracted features in the plot to show the different decision boundaries for each possible interfering gas that have been detected. The idea behind using both techniques (i.e., composite dimensions) is to make it easier to detect a false positive, as well as providing some diagnostic information to the user by identifying what gas is being detected. The different regions (1021-1029) show how the different types of interfering gases may be detected through the pre-trained gas sensor 104. FIG. 10 shows both the real OGE region 1010 versus the several false positives (non-OGE) regions (1021-1029), including decision boundaries that enable the ML or DL algorithm to identify the false positive interfering gases.

FIGS. 11A and 11B depict an exemplary flow diagram to pre-train the gas sensor 104 by a plurality of known gas analyte, and utilizing a Machine Learning (ML) algorithm. For example in step 1102, for each known gas analyte, raw signals 104a such as resistance and capacitances may be generated from the multi-electrodes 104b of the gas sensor 104 and sent to the processor for features extraction (e.g., changes in impedance or transfer function over time duration) in step 1104. The features extraction step 1104 may include time-frequency transformation (such as discrete cosine transformation DCT or discrete Fourier transformation DFT) to transform time domain analog signals into frequency domain signals. In step 1106, the extracted features may be organized according. In step 1108 machine learning (ML) algorithms are applied to the organized data to establish a candidate model 1110 (such as multi-dimensional decision boundaries construction). By repeating steps 1102 to 1110 for the remaining of the plurality of known gas analyte, the Candidate model 1110 may be updated (see step 1111) to establish a database or to build a composite decision boundaries plot to complete the ML algorithm 108a training which is stored in the memory 108 to be executed by the processor 106. FIG. 11B shows the details of the ML learning step 1108 in FIG. 11A. More specifically, step 1108 may be accomplished by repeating training steps 1108a to 1108n. Each of the training steps (e.g., 1108a) may include sequentially carrying out the operations of: convolution, rectified linear unit (ReLU) and pooling operations. The Deploy model 1112 would be a field ready ML algorithm when working in conjunction with the multi-electrode gas sensor 104 to perform gas analyte classifications.

Figure 13:
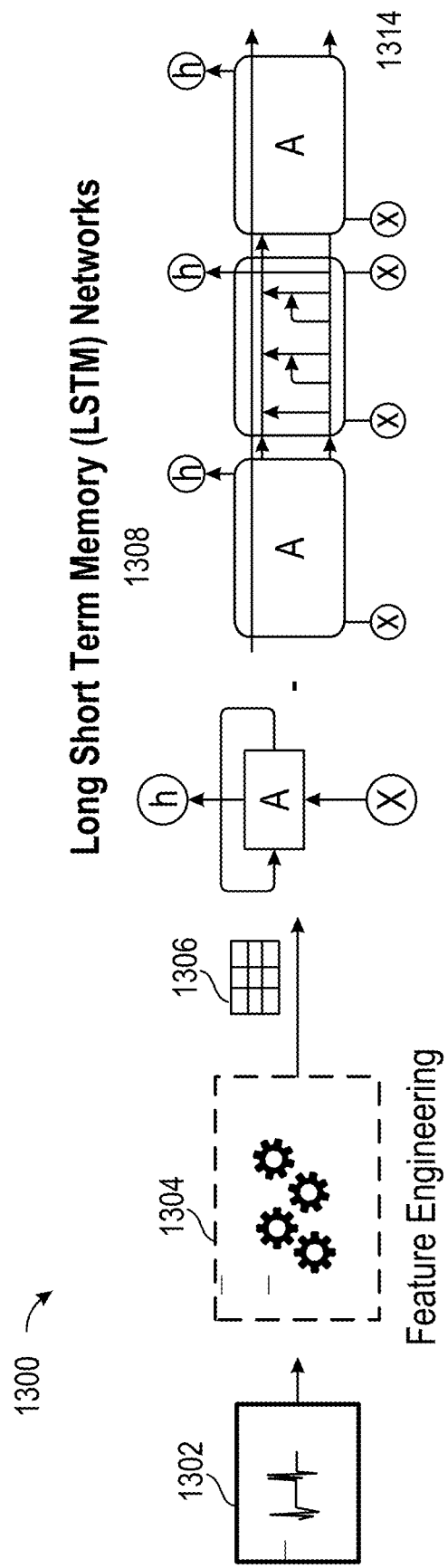
FIG. 13 depicts implementing Long Short-Term Memory (LSTM) Neural Network in DL training.

Likewise these desired classifications may be achieved with deep learning (DL) algorithms, as depicted in FIGS. 11A, 11B, utilizing pre-trained convolution neural networks (e.g., Convolutional Neural Network CNN and Long Short-Term Memory (LSTM)) and automatic signal feature extraction as shown in FIGS. 12 and 13.

Figure 14:
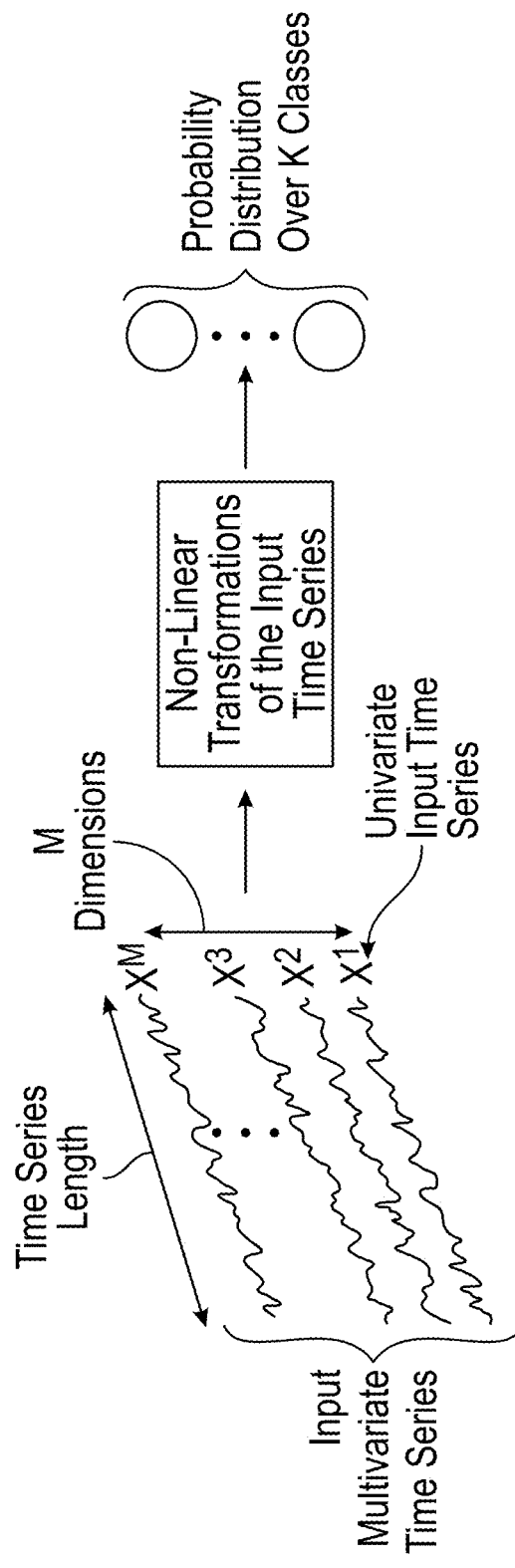
FIG. 14 depicts a DL framework for time series classification.
Figure 15:
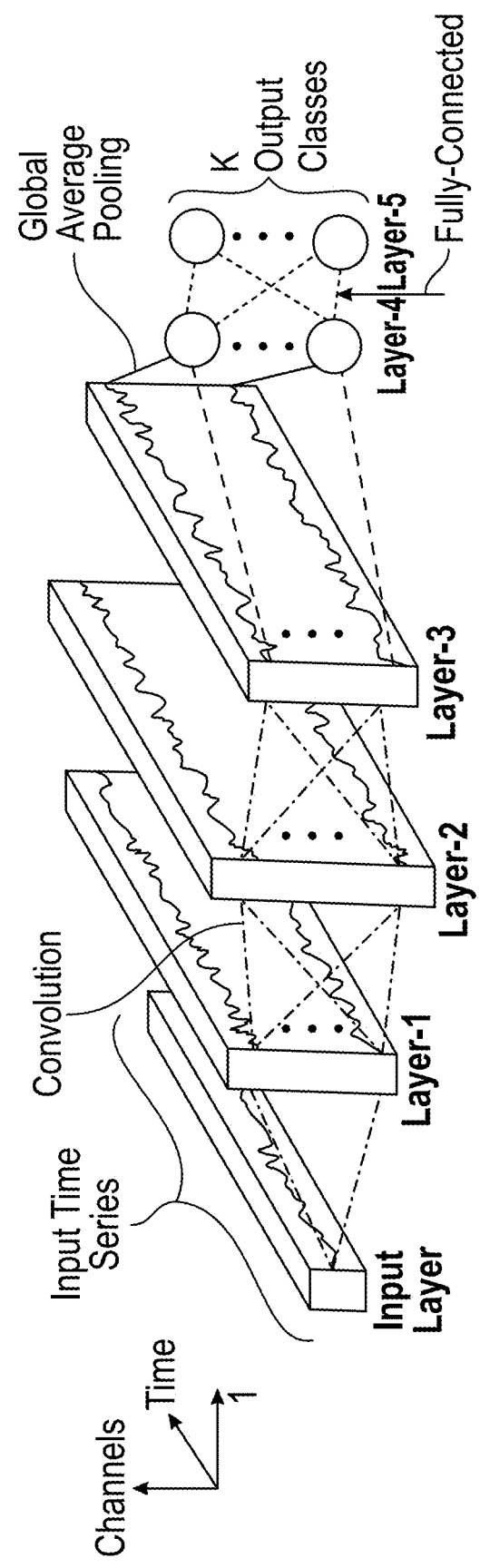
FIG. 15 depicts an example of a Convolutional Neural Network architecture to carry out a DL algorithm.

FIG. 14 illustrates an example of DL framework for time series classification. FIG. 15 depicts an example of a Convolutional Neural Network architecture to carry out a DL algorithm pre-training using the extracted features. The deep learning (DL) algorithm may consist of multiple layers (See FIGS. 14, 15) that implement nonlinear functions. Each layer may receive as an input from the output of a previous layer and applying a nonlinear transformation that computes its output (i.e., sequential pipeline processing technique). These nonlinear transformations may be determined by the trainable parameters in the fitting process. Some deep learning architectures that may be implemented may include the Convolution Neural Networks (see FIG. 11B), Inception Time, and Echo State Networks.

While particular examples above have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method comprising:
   monitoring, at least one gas analyte released by a gas source, by at least one gas sensor having one or more sensing electrodes, wherein the at least one gas sensor having been pre-trained a priori utilizing one of a Machine Learning (ML) or a deep learning (DL) algorithm before an initial field deployment of the at least one gas sensor to classify the at least one gas analyte released by the gas source being an event comprising one or both of: an off gas event (OGE) or a thermal run away event (TRE) from a non-OGE interfering gas release, and
   wherein the utilizing of the ML or DL algorithm to pre-train the at least one gas sensor a priori to classify the at least one gas analyte released by the gas source comprising:
   training the at least one gas sensor to detect over a time duration, each and every of a plurality of known gas analytes that can be potentially released by the gas source, by each of the one or more sensing electrodes of the at least one gas sensor to generate respective sensor signals that represent unique characteristics of the each and every of the plurality of known gas analytes;
   pre-processing over the time duration, the generated respective sensor signals in order to extract corresponding plurality of features of the each and every of the plurality of known gas analytes;

processing the extracted corresponding plurality of features to establish a decision boundary of false positive release for one or both of the OGE and TRE, and to establish respective decision boundary for remaining each and every non-OGE type of interfering gas release; and storing the established decision boundaries in the ML or DL algorithm into a memory as one or more candidate model for sensor's post field deployment in order to classify the at least one gas analyte released by the gas source as being one or both of the OGE or the TRE from the non-OGE interfering gas release.

2. The method according to claim 1, wherein the gas source comprises a rechargeable Lithium ion battery system or an electric energy storage system, wherein the OGE or the TRE comprising detection of release of any one of or a combination of at least the following flammable or toxic gases: lithium-ion battery off gas, dimethyl carbonate, diethyl carbonate, methyl ethyl carbonate, ethylene carbonate, propylene carbonate, vinylene carbonate, carbon dioxide, carbon monoxide, hydrocarbon, methane, ethane, ethylene, propylene, propane, benzene, toluene, hydrogen, oxygen, nitrogen oxides, volatile organic compounds, toxic gases, hydrogen chloride, hydrogen fluoride, hydrogen sulfide, sulfur oxides, ammonia, and chlorine.

3. The method according to claim 1, wherein when the respective gas sensor signals generated by each of the one or more sensing electrodes of the at least one gas sensor comprise impedance values based on an equivalent impedance circuit model having a first parallel resistor and capacitor pair cascading in series with a second parallel resistor and capacitor pair.

4. The method according to claim 3, wherein the first parallel resistor and capacitor pair in the equivalent circuit model simulates dynamics of the at least one gas sensor responses when exposed to a combination of different released analyte gases.

5. The method according to claim 4, wherein the impedance equivalent circuit model of the sensor further comprising cascading in series, contact resistance to the first parallel resistor and capacitor pair.

6. The method according to claim 5, further comprising calculating for a given fixed input voltage V and at a given impedance value R, an input/output transfer function for the gas sensor in a LaPlace domain (s), wherein the input/output transfer function is expressed as follows:

$$\frac{R}{V}(s) = \frac{(CPE*CsRnRs)s^2 + (CPE*Rn + Cs*Rs)s + 1}{CPE*C_sR_cR_nR_ss^2 + (CPE*RcRn + CPE*RnRs + CsRcRs + CsRnR)s + Rc + Rn + Rs}$$

wherein Rc is a contact resistance, Rn is a first parallel resistance, Rs is a second parallel resistance, and CPE is an equivalent capacitance of gains to describe a general second order RC circuit.

7. The method according to claim 1, wherein the detecting of the at least one gas analyte released by the gas source by the at least one gas sensor having been pre-trained by the ML or DL algorithm eliminates use of a reference sensor.

8. The method according to claim 1, wherein the ML or DL algorithm pre-training of the at least one gas sensor in detecting the at least one gas analyte released by the gas source further comprising distinguishing the sensor impedance changes due to environmental disturbances caused by one or more of: temperature changes, relative humidity changes, and other gases that effects a partial pressure of oxygen in the environment that leads to reporting a false positive.

9. The method according to claim 1, wherein the ML algorithm pre-training of the at least one gas sensor in the extraction of the corresponding plurality of features of the each and every of the plurality of known gas analytes comprising utilizing any one of or a combination of features comprising: moving average calculation, Bollinger band, minimum electrode impedance, maximum rate of impedance change, maximum rate of recovery of impedance for each of the at least one electrodes on the at least one gas sensor, principal component analysis (PCA), linear discriminant analysis, wherein the DL algorithm pre-training of at least at least one gas sensor in the extraction of the corresponding plurality of features in the each and every of the plurality of known gas analytes are contained internally in hidden layers of Neural Networks.

10. The method according to claim 1, wherein the ML or DL algorithm pre-training of the at least one gas sensor in the establishing of the decision boundary of false positive release for the OGE or the TRE and respective decision boundary for the remaining each and every type of non-OGE interfering gas release, comprising evaluating the generated sensor signals utilizing any one of determination methods comprising: Support Vector Machines, Discriminant Analysis or nearest neighbor algorithm, Naïve Bayes and Neural Neighbor, Linear Regression, GLM, Support Vector Regression, GPR, Ensemble Methods, Decision Trees, and DL Neural Networks comprising at least one of: Convolution Neural Networks (CNN), Inception Time Architecture, Echo State Network, and Long Short Term Memory (LSTM) Networks.

11. A system comprising:
an enclosure having a gas source; and
at least one gas sensor having one or more sensing electrodes that is deployed to monitor at least one gas analyte released by the gas source, wherein the at least one gas sensor before the deployment, having been pre-trained a priori utilizing one of a Machine Learning (ML) or deep learning (DL) algorithm that is stored as program code in a memory for execution by a processor in order to detect and classify the at least one gas analyte released by the gas source being an event comprising one or both of: an off gas event (OGE) or a thermal run away event (TRE) from a non-OGE interfering gas release,
wherein the utilizing of the ML or DL algorithm to pre-train the at least one gas sensor a priori to classify the at least one gas analyte released by the gas source causes the processor to pre-train the at least one gas sensor before sensor's initial field deployment to:
detect over a time duration, each and every of a plurality of known gas analytes that can be potentially released by the gas source, by each of the one or more sensing electrodes of the at least one gas sensor to generate respective sensor signals that represent unique characteristics of the each and every of the plurality of known gas analytes;
pre-process over the time duration, the generated respective sensor signals in order to extract corresponding plurality of features of the each and every of the plurality of known gas analytes;
process the extracted corresponding plurality of features to establish a decision boundary of false positive release for one or both of the OGE and TRE, and to establish respective decision boundary for remaining each and every non-OGE type of interfering gas release; and store the established decision boundaries in the ML or DL algorithm into a memory as one or more candidate model for sensor's post field deployment in order to classify the at least one gas analyte released by the gas source as being one or both of the OGE or the TRE from the non-OGE interfering gas release.

12. The system according to claim 11, wherein when the respective gas sensor signals generated by each of the one or more sensing electrodes of the at least one gas sensor comprise impedance values based on an equivalent impedance circuit model having a first parallel resistor and capacitor pair cascading in series with a second parallel resistor and capacitor pair and the first parallel resistor and capacitor pair in the equivalent circuit model simulates dynamics of the at least one gas sensor responses when exposed to different released gases.

13. The system according to claim 12, wherein the detecting of the at least one gas analyte released by the gas source by the at least one gas sensor having been pre-trained by the ML or DL algorithm eliminates use of a reference sensor.

14. The system according to claim 11, wherein the ML or DL algorithm pre-training of the at least one gas sensor in the extraction of the corresponding plurality of features of the each and every of the plurality of known gas analytes comprising utilizing any one of or a combination of: moving average calculation, Bollinger band, minimum electrode impedance, maximum rate of impedance change, maximum rate of recovery of impedance for each of the at least one electrodes on the at least one gas sensor, principal component analysis (PCA), linear discriminant analysis.

15. The system according to claim 11, wherein the ML or DL algorithm pre-training of the at least one gas sensor in the establishing of the decision boundary of false positive release for the OGE or the TRE and respective decision boundary for the remaining each and every type of non-OGE interfering gas release, comprising evaluating the generated sensor signals utilizing any one of determination methods comprising: Support Vector Machines, Discriminant Analysis or nearest neighbor algorithm, Naïve Bayes and Neural Neighbor, Linear Regression, GLM, Support Vector Regression, GPR, Ensemble Methods, Decision Trees, and DL Neural Networks comprising at least one of: Convolution Neural Networks (CNN), Inception time architecture, Echo state Networks, and Long Short Term Memory (LSTM) Networks.

* * * * *